United States Patent [19]

Heilmann et al.

[11] Patent Number: 5,760,152

[45] Date of Patent: Jun. 2, 1998

[54] CROSSLINKED ISOCYANATE FUNCTIONAL POLYMER SUPPORTS

[75] Inventors: Steven M. Heilmann, Afton; Gary J. Drtina, Woodbury; Louis C. Haddad, St. Paul; Frederick W. Hyde, New Brighton; Dean M. Moren, North St. Paul; Robert A. Pranis, St. Paul, all of Minn.

[73] Assignee: Minnesota Mining and Manufacturing Company, St. Paul, Minn.

[21] Appl. No.: 453,316

[22] Filed: May 30, 1995

Related U.S. Application Data

[62] Division of Ser. No. 7,344, Jan. 21, 1993.

[51] Int. Cl.$^6$ .................................................. C08F 26/02
[52] U.S. Cl. ................. 526/301; 526/303.1; 526/317.1; 526/318; 526/319; 435/177; 435/180; 264/319; 264/330; 264/331.15; 264/331.18; 264/331.19; 264/331.21; 528/48; 528/50; 528/75; 528/85
[58] Field of Search ........................... 435/177, 180; 264/319, 330, 331.55, 331.18, 331.19, 331.21; 526/301, 303.1, 317.1, 318, 319; 528/48, 50, 75, 85

[56] References Cited

U.S. PATENT DOCUMENTS

| 3,694,416 | 9/1972 | Rubens et al. | 260/77.5 TB |
|---|---|---|---|
| 4,237,229 | 12/1980 | Hartdegen | 435/182 |
| 4,582,805 | 4/1986 | Bozzelli et al. | 435/180 |
| 5,200,471 | 4/1993 | Coleman et al. | 525/326.9 |

FOREIGN PATENT DOCUMENTS

A 35 01 493  1/1985  Germany.

OTHER PUBLICATIONS

Database WPI Week 8437, Derwent Publications Ltd., London, GB; AN 84-228359 & JP-A-59 135 887 (4 Aug. 1984) (abstract).

*Primary Examiner*—W. Robinson H. Clark
*Attorney, Agent, or Firm*—Gary L. Griswold; Walter N. Kirn; Lorraine R. Sherman

[57] ABSTRACT

Insoluble supports are prepared which possess high surface areas and efficiently dispersed isocyanate groups. These reactive supports are useful for covalently binding proteins which preferably are enzymes and provide catalysts for conducting organic reactions.

23 Claims, 1 Drawing Sheet

CROSSLINKED ISOCYANATE FUNCTIONAL POLYMER SUPPORTS

This is a division of application Ser. No. 08/007,344 filed Jan. 21, 1993.

FIELD OF THE INVENTION

This invention relates to crosslinked isocyanatefunctional polymer supports and a method for their preparation. In another aspect, biomacromolecules (especially proteins) are covalently bound to the crosslinked isocyanate-functional supports of the invention to form support/biomacromolecule conjugates. The resultant support/biomacromolecule conjugates are useful for bioseparations or as catalysts for conducting synthetic organic reactions.

BACKGROUND OF THE INVENTION

Proteins are exceedingly versatile biomacromolecules. One class of proteins, known as enzymes, probably functions as nature's most effective catalysts for conducting complex organic syntheses.

Because enzymes function so efficiently at low concentrations causing a high conversion of reactants to products under extremely mild conditions of temperature and pH and do so with an incomparable degree of specificity (in terms of functional groups affected), they have long been sought after as catalysts by organic chemists to conduct chemical reactions. Medicinal and pharmaceutical chemists have further been intrigued by the ability of enzymes often to synthesize just one of the possible optical isomers of a compound wherein the simple spatial arrangement of four different substituents on a particular carbon atom gives rise to unique pharmacological behavior. Interest in enzymes for synthetic purposes has also heightened recently by advances in molecular genetics that have allowed for the preparation of specific enzymes in a highly purified state, on a relatively large scale, and at substantially reduced cost.

Insolubilization of enzymes without losing catalytic activity has been an objective of many investigators because of the very practical and obvious advantage that the catalyst system can be easily removed from the reaction mixture by simple filtration. Furthermore, although immobilization may seem "unnatural" for an enzyme, immobilized or heterogeneous conditions are frequently encountered by enzymes in their native state in vivo since enzymes are often physically located (literally immobilized) at interphases between aqueous and lipid regions within cell organelle structures.

Enzymes have traditionally been immobilized onto insoluble supports by three methods: 1) non-covalent adsorption by hydrophobic or ionic attraction to the support; 2) entrapment within a polymer matrix; and 3) by covalent attachment. Leaching or loss of the enzyme from the support is a serious problem and is often encountered with the adsorption and entrapping methods. Leaching results in physical losses of bound enzyme, normally the most expensive component of the system, and increased separation costs as well because the product solution is contaminated with free enzyme. Covalent attachment generally provides the lowest degree of enzyme leaching and often results as well in increased catalyst lifetime because of enhanced stabilization of the enzyme. Disadvantages of covalent methods include complexity of the chemical operations required to bind the enzyme and, more importantly, the relatively low degrees of catalytic efficiencies, e.g., 10–15%, often observed for bound enzymes compared to free enzymes.

Covalent attachment of enzymes to reactive supports has generally involved reaction of nucleophilic 4-aminobutyl groups of lysine residues within an enzyme's structure and electrophilic groups present on a support. A wide variety of electrophilic groups have been employed on supports for binding including azlactone, oxirane, cyanate, sulfonyl chloride, carbonyl imidazole, isothiocyanate, and isocyanate. Of the electrophilic groups listed, isocyanate is perhaps the most reactive and most desirable for protein binding, provided hydrolysis or reaction with the water solvent does not seriously compete with reaction by lysine residues. Hydrolysis is not only wasteful of isocyanate groups for binding but ultimately produces amine groups which become protonated and positively charged at useful binding pHs. Attraction of negative charges on the enzyme can result in temporary binding to this positively charged support via an ionic bond. However, if the pH or ionic strength of the medium is subsequently altered, ion exchange can occur and the enzyme will be released, i.e., leached, from the support.

An accepted tenet in the practice of binding enzymes to supports is that lipophilicity of the backbone support plays an important role in the overall activity and stability of the bound enzyme catalyst. Therefore, control and manipulation of support lipophilicity is important and may vary for a given enzyme. The simple procedure of changing the nature and relative amounts of hydrophilic and hydrophobic monomers in a free radical addition polymerization is especially conducive to efficient control of support lipophilicity. By contrast, lipophilicity control with step growth polymers such as polyurethane and olyureas is not as easily achieved, especially when formation of support and protein binding from water are accomplished simultaneously.

Bozelli, et al., in U.S. Pat. No. 4,582,805 disclose thermoplastic, e.g., organic solvent soluble (uncrosslinked), homo- and copolymers of vinyl addition monomers containing isocyanate groups useful for immobilizing biological materials.

SUMMARY OF THE INVENTION

Briefly, the present invention provides an insoluble polymer support comprising isocyanate groups dispersed on a crosslinked polymeric backbone derived from ethylenically-unsaturated monomers by free radical polymerization.

In another aspect, there is also provided an insoluble polymer support comprising the copolymerized reaction product of at least one ethylenically-unsaturated isocyanate-functional monomer, a polyethylenically-unsaturated crosslinking monomer, and a free radical initiator. Such isocyanate-functional polymer supports are prepared in the presence of crosslinking monomers which control the overall availability of isocyanate groups on the support and, optionally, in the presence of other acrylic monomers which control the overall lipophilicity of the support.

In yet another aspect, the present invention provides an insoluble supported catalyst comprising an insoluble polymer support comprising isocyanate groups or hydrolysis products thereof dispersed on a crosslinked polymeric backbone derived from ethylenically-unsaturated monomers by free radical polymerization and having at least one biomacromolecule, preferably a protein, covalently bound thereto.

In a further aspect, a method is disclosed for catalyzing a reaction of complimentary reactants using the supported catalyst of the invention. Complementary reactants are any coreactants, the reaction of which is catalyzed by the supported catalysts of the invention.

The polymer supports of the present invention have a relatively high surface area for efficient covalent binding of proteins, which preferably are enzymes, from aqueous solution with little concomitant hydrolysis. As a result, insoluble catalysts are provided having efficiently bound proteins that retain high levels of catalytic activity and are stable for prolonged usage.

Reaction Equations, below, summarize preparation of the polymer support and supported catalyst of the invention.

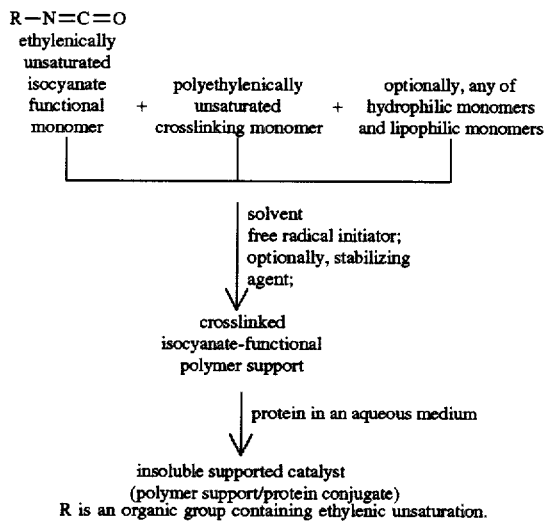

In this application:

"alkyl" means the monovalent residue remaining after removal of one hydrogen atom from a linear or branched chain hydrocarbon having 1 to 20 carbon atoms;

"lipophilic" means "lipid-loving" and has broad connotations and relationships to terms used in the art and in this application can be used interchangeably with "hydrophobic";

"hydrophobic attraction" means lipophilic groups on a protein interact with a lipophilic support; this is similar to a solubility principle in which like dissolves (interacts with) like.

Proper definition and control of lipophilicity of the support is important for effective catalyst construction in the present invention. Isocyanate-functional polymer supports (and binding protocols described herein) rapidly engage in hydrophobic binding of proteins and subsequently undergo covalent attachment of the protein by reaction of support isocyanates with nucleophilic groups, e.g., amine, hydroxyl, and thiol, on the protein. The unproductive side reaction with the water solvent occurs to a much lesser extent with the supports of the invention.

Catalysts for organic syntheses are thus created that can be prepared straightforwardly, possess high levels of activity, and do not release protein into reaction product solutions.

The present invention provides insoluble isocyanate-functional supports in which the isocyanate groups are readily available for covalently binding proteins, which preferably are enzymes, from an aqueous solution to provide an insoluble catalyst. The catalyst comprises an efficiently immobilized enzyme which provides a high degree of catalytic activity and a stable environment for the protein.

In contrast to the present invention, the aforementioned uncrosslinked isocyanate-functional polymers and copolymers of Bozelli ('805) are employed dissolved in an organic solvent as more or less an adhesive to bind bacterial cells together and not as an actual reactive, insoluble support from which enzymes may be bound as in the present invention. Bozelli, et al., do not contemplate crosslinked, isocyanate-functional supports or the use of relatively high concentrations of water in an enzyme binding operation.

DETAILED DESCRIPTION OF THE INVENTION

Figure 1:
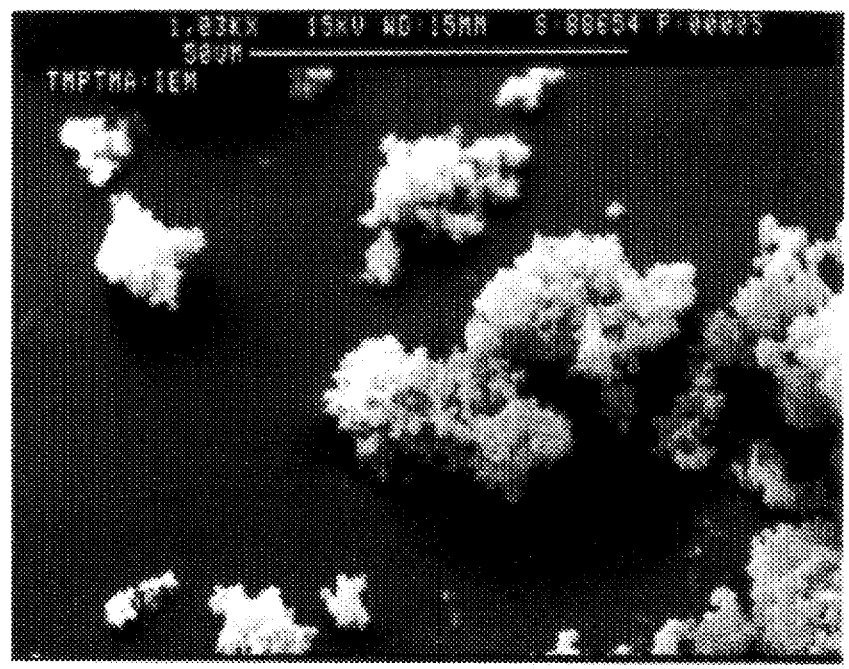
FIG. 1 is a scanning electron micrograph of a polymer support of the present invention magnified 103,000× (identified in Example 1, below as T/20).

This invention provides crosslinked isocyanate-functional polymer supports in which the isocyanate groups are effectively dispersed on the support to covalently bind relatively high levels of enzymes providing highly active, insoluble catalysts for conducting organic reactions. The novel polymer supports of the invention result from the copolymerization of the following monomers:

i) from 1 to 99 parts (by weight) of isocyanate-functional monomers;

ii) from 99 to 1 parts of crosslinking monomers; and iii) from 0 to 98 parts of other copolymerizable monomers.

The polymerization methods employed to synthesize the reactive supports of the invention are "dispersion" and "precipitation" polymerizations. These methods, more fully described by R. Arshady, *J. Microencansulation*, 1988, 5, 101–114, involve precipitation of propagating polymers from media which originally served as solvent for both monomers and initiator. Initiation and propagation occur chiefly in solution, although primary propagation can occur on the precipitated particles because polyethylenically unsaturated crosslinking monomers are utilized, and many suitable crosslinking monomers have more than two polymerizable functionalities. Useful stabilizing agents for dispersion polymerizations include reaction products of allyl alcohol, 3-hydroxypropyl acrylate, or 2-hydroxyethyl methacrylate (preferred) and alkyl copolymers of acrylates/ methacrylates and 2-vinyl-4,4-dimethylazlactone; these materials are described more fully in U.S. Pat. No. 4,304, 705, which is incorporated by reference. Other useful stabilizing agents include hydrophilic polymers such as poly (N-vinylpyrrolidinone) and hydroxyethylcellulose and hydrophobic polymers such as copoly(iso-octyl acrylate-:acrylic acid) (90:10). Desirable levels of the stabilizers are from 1 to 20 weight percent, preferably 5 to 15 weight percent. While no particular benefit or effect on polymer support particle size has been observed by inclusion of stabilizers, the stabilized polymeric particles seem to better accept surfactants and are more easily "wetted"0 during subsequent protein binding from aqueous solution. The dispersion polymerization method therefore is preferred.

Suitable isocyanate-functional monomers used singly or in combination are polymerizable ethylenically-unsaturated isocyanate functional monomers which preferably include isocyanatoalkyl esters of ethylenically unsaturated carboxylid acids such as 2-isocyanatoethyl methacrylate and 2-isocyanatoethyl acrylate; and acryloyl isocyanates such as methacryloyl isocyanate. 2-Isocyanatoethyl methacrylate (IEM) is preferred. Quantities of these monomers (based on 100 parts by weight total monomers) in the support formulation can range from 1 to 99 parts; preferably, 1 to 25 parts; more preferably 5 to 20 parts; and most preferably, 7 to 12 parts. Very high amounts of isocyanate-functional monomers are generally unnecessary for protein binding and the probability of hydrolysis/anion exchange is actually increased.

Suitable monomers, used singly or in combination, which provide crosslinking capability because of at least two ethylenically unsaturated moieties include polyethylenically-unsaturated esters, preferably of at least one of acrylic acid and methacrylic acid, such as ethylene glycol dimethacrylate (EGDMA), trimethylolpropane trimethylacrylate (TMPTMA), pentaerythritol tetraacrylate, pentaerythritol trimethacrylate, dipentaerythritol hydroxypentaacrylate (DPEHPA), 1,6-hexanediol diacrylate, and 1,4-butanediol dimethylacrylate; polyethylenically-unsaturated amides such as methylenebis(acrylamide), methylenebis(methacrylamide), N,N'-dimethacryloyl-1,2-diaminoethane, and bis(methacrylamidomethyl) ether; and polyvinyl benzene derivatives such as 1,3- and 1,4-divinylbenzene. Polyethylenically-unsaturated esters are preferred. Quantities of the crosslinking monomers in the supports range from 1 to 99 parts. In many instances an open, relatively non-swelling (in water or organic solvents) filamentous structure possessing a high surface area is desired, and useful concentrations are generally in excess of 30 parts by weight preferably in excess of 40 parts by weight, with the specific lower limit for non-swelling of the filaments within the overall solvated structure being somewhat variable depending on the crosslinking monomer employed.

Other monomers which are different from the crosslinking and isocyanate functional monomers described above may optionally be included in the supports of the invention are generally added to manipulate the lipophilicity of the support. Mention has already been made of the importance of lipophilicity control of the supports to facilitate hydrophobic binding, to increase catalytic activity, and to increase useful lifetimes of, for example, enzyme catalysts. Other monomers are of two general types: hydrophilic and lipophilic. Suitable hydrophilic monomers used singly or in combination in the invention include: N,N-dimethylacrylamide (DMA), N-vinylpyrrolidinone, 2-hydroxyethyl methacrylate (HEMA; although potentially reactive with the isocyanate-functional monomers, comparative runs at appropriate dilution in heptane show no reaction with IEM after 2 hours at 70° C.) and 2-acetoxyethyl methacrylate (HEMAC); DMA and HEMA are preferred. Lipophilic monomers used singly or in combination include: n-butyl methacrylate (BMA), iso-butyl methacrylate (IBMA), methyl methacrylate (MMA), 2-phenoxyethyl methacrylate (PhOEM), cyclohexyl methacrylate (CYMA), and lauryl methacrylate (LMA).

Common free radical initiators can be employed which include those known in the art such as azobis(isobutyronitrile) (AIBN), benzoyl peroxide, lauryl peroxide, t-butyl peroxypivalate, and azobis(1-cyclohexanecarbonitrile) in concentrations of from 0.5 to 5.0 weight percent (based on total monomers), preferably from 1.0 to 3.0 weight percent. As is apparent to one skilled in the art of free radical polymerizations, a non-oxygenated atmosphere is highly desirable, so the system is purged to remove oxygen with a suitable inert gas such as nitrogen or argon. Polymerization temperatures and times required are dependent on the initiator selected and should be adjusted to allow homolytic cleavage of the initiator so that polymerization can commence quickly. With AIBN (2.0 weight percent), for example, temperatures of about 70° C. are effective for promoting the polymerization and obtaining a high conversion, e.g., >98 percent, of monomers to support polymer in about 2 hours from the onset of particle precipitation. The support particles can then be isolated by filtration, washed with non-reactive organic solvents listed below, and dried conventionally at reduced pressure and/or elevated temperatures.

The nature of the polymerization solvent is important, primarily with regard to the density of the final support structure. In generally "poor" solvents for a propagating polymer, such as heptane or hexane, precipitation occurs very early in the propagation phase and results in a more open support structure possessing a relatively high surface area and low density. On the other hand, when the solubility parameters are more closely matched, i.e., when the "goodness" of the solvent for the polymer is better, precipitation occurs later and a support with a higher density results. Selection of the polymerization solvent can therefore be used to tailor the physical makeup of the support to fit a particular application. When the isocyanate functionality is desired to be at a very high level and efficiently dispersed in an open structure such as might be employed in a column or plug-flow system, heptane can be the solvent of choice. Alternatively, when a more dense structure can lead to improved physical strength and faster settling properties which are desirable for a heterogeneous catalyst employed in stirred tank reactors, toluene, tetrahydrofuran, or ethyl acetate may be better choices for polymerization solvents.

Besides serving as solvent for all the monomers employed in a particular formulation, an additional requirement is that the solvent be unreactive with the isocyanate functionality and other monomers and with the polymeric product. Useful organic solvents used singly or in combination include hexane, heptane, the Isopar™ hydrocarbon solvents (available from Exxon, Houston, Tex.), toluene, xylene, 1,2-dichloroethane, tetrahydrofuran, ethyl acetate, butyl acetate, amyl acetate, methyl ethyl ketone, and acetonitrile. The weight ratio of total monomers to solvent employed is generally 1:5 to 1:10. It is desirable that the concentration of monomers be as high as possible to facilitate high conversion, but especially with solvents which contribute towards a relatively open, low density polymer structure, it may be necessary to add small portions of additional solvent to facilitate good mixing during the polymerization period. Stirring should be efficient; rates with overhead paddle-type stirrers of 300 rpm or higher are desirable.

The crosslinked isocyanate-functional polymer supports (which generally are agglomerated structures) of the invention have particle sizes (largest diameter) in excess of 10 micrometers, preferably in the range of 20 to 1000 micrometers. The agglomerated structures which to the naked eye appear as a powder can be cluster-like or filamentous and can comprise from one to 500 or more regularly or irregularly shaped beads.

Useful isocyanate-functional polymer supports of the invention have surface areas greater than 20 square meters per gram and up to 400 square meters per gram, preferably in the range of 50 to 350, and most preferably 100 to 300 square meters per gram.

Isocyanate-Functional Polymer Supports

The following procedure for the preparation of a TMPTMA:IEM (80:20) support is illustrative:

A three liter, three-necked, round bottomed flask equipped with a mechanical stirrer, thermometer, gas inlet, dropping funnel, and condenser was charged with TMPTMA (80.0 grams; available from Sartomer Co., Inc., Exton, Pa.), IEM (20.0 grams; purchased from Dow Chemical Co., Midland, Mich.), 1.67 grams of a stabilizer solution [33% solids in Isopar G; consisting of a lauryl methacrylate:2-vinyl-4,4-dimethylazlactone (94:6 w/w) copolymer reacted with HEMA], and heptane (800 mL). The solution was stirred (500 rpm) and sparged with nitrogen for 10 minutes before warming to 70° C.

AIBN (2.5 grams; available from Polysciences, Inc., Warrington, Pa.) was added to the hot solution, and within a few minutes particles were visible in the reaction vessel. As the polymerization proceeded, seven 100 mL portions of deoxygenated heptane were added at various time to facilitate mixture. After 2 h from the detection of particles, the reaction mixture, now a white creamy flocculant polymer mass, was allowed to cool. The solid was filtered and washed with heptane. The polymer product was then placed in a 4 L beaker and covered with a solution consisting of 1200 mL of ethyl acetate and 1.0 gram of Pluronicm™ L-31 polyalkylene oxide surfactant (available form BASF, Parsippany, N.J.) (this washing operation conducted with occasional stirring removed unreacted monomers and minimized static electricity problems with the eventual dry support). After 1 hour, the mixture was filtered, and the polymeric filtercake was dried to constant weight at 70° C. under an atmosphere of dry nitrogen for 19 h, followed by 3 h at <1 Torr. The polymer weighed 97.8 grams (97.8 % yield) and possessed a surface area (BET method) of 134 $m^2/g$. The shorthand notation or designation for the support is "T/20".

Figure 2:
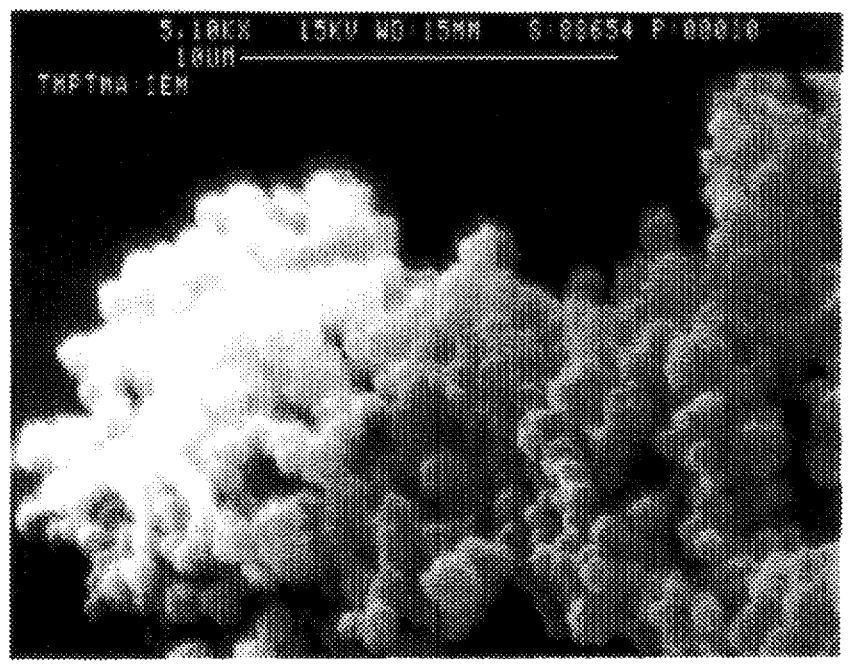
FIG. 2 is a scanning electron micrograph of the polymer support of FIG. 1 magnified 510,000×.

Scanning electron micrographs of T/20 are shown in FIGS. 1 and 2. To the naked eye the polymer support resembles a fine grained powder. Under magnification, each grain appears to be a cluster of beads, typically about 1 micrometer in largest dimension. This accounts for the very high surface area of the polymer support which is generally white or off-white in color. Other supports prepared in this fashion were the following:

| Support | Designation | Surface Area ($m^2/g$) |
|---|---|---|
| TMPTMA (100) | T | 168 |
| TMPTMA:IEM:LMA (70:10:20) | T/10LMA-20 | 81 |
| TMPTMA:IEM:BMA (60:20:20) | T/20BMA-20 | 64 |
| TMPTMA:IEM:BMA (70:20:10) | T/20BMA-10 | 136 |
| TMPTMA:IEM:HEMAC (83.5:5:11.5) | T/5HEMAC-11.5 | 166 |
| TMPTMA:IEM:HEMAC (82.4:10:7.6) | T/10HEMAC-7.6 | 155 |
| TMPTMA:IEM:HEMAC (81:15:4) | T/15HEMAC-4 | 120 |
| TMPTMA:IEM:DMA (80:10:10) | T/10DMA-10 | 130 |
| TMPTMA:IEM:PHOEM (40:10:50) | T/10PHOEM-50 | 48 |
| TMPTMA:IEM:DMA (70:15:15) | T/15DMA-15 | 89 |
| TMPTMA:IEM:DMA (60:20:20) | T/20DMA-20 | 73 |
| EGDMA:IEM (80:20) | E/20 | 116 |
| TMPTMA:IEM:HEMA (50:20:30) | T/20HEMA-30 | 84 |
| DPEHPA:IEM[a] | D/20 | 345 |
| (80:20) Comparative Supports | | |
| MMA:IEM (80:20) | 20MMA-80 | 9 |
| IEM:MMA (40:60) | 40MMA-60 | 8 |
| IEM:DMA (80:20) | 80DMA-20 | 4 |

[a]= Dispersion polymerization was conducted using ethyl acetate as solvent.

Covalent Binding of Proteins, preferably Enzymes to Isocyanate-Functional Supports As alluded to earlier, an objective of the binding procedure is to challenge the enzyme dissolved in an aqueous medium with a support of the invention possessing a lipophilicity such that essentially all of the enzyme is initially hydrophobically bound onto the support; covalent binding takes place at a somewhat slower rate and is believed to be completed within a few hours, e.g. 2–4 hours, at room temperature. Ideally, the support should be hydrophilic from the standpoint of enhancing the isocyanate group's reactivity (due to polarity and/or local concentration effects) to facilitate covalent binding but not too hydrophilic because the support can become so reactive that hydrolysis competes, ultimately giving rise to reversible ionic binding and leaching. Also, extremely hydrophilic supports become less attractive to the enzyme in the necessary hydrophobic binding step. At the opposite extreme, if the support becomes too lipophilic, hydrophobic binding will occur but the isocyanate's reactivity may be diminished to such a point that covalent binding will not occur, and the result will again be leaching of the unstable hydrophobically bound enzyme from the support; also, because of the excessively lipophilic environment even bound enzyme will be less active and less staple.

Recommended binding procedures or protocols are designed to account for the above factors favoring the covalent binding process. First, the enzyme is initially dissolved in high concentrations of olyanionic buffered salt solutions such as are disclosed in PCT International Publication No. WO 92/07879. The purpose of the polyanionic salt is to almost "salt out" the enzyme so that it will readily engage in hydrophobic binding with the organic polymer supports of the invention. Useful bound protein concentrations are in the range of 1 to 20 weight percent based on the dry weight of the support, preferably 3 to 10 weight percent. Useful polyanionic salts include inorganic salts such as sodium sulfate and alkali metal salts of organic acids such as malonic, maleic, tartaric, and citric acids. The preferred organic salt is sodium citrate.

Following the hydrophobic and covalent binding operations which both take place generally within 2–4 hours at ambient temperatures (typically 20°–25° C.), as a further precaution to eliminate leaching, all non-covalently bound enzyme can be washed from the support by application of an aqueous surfactant solution. Suitable surfactants are determined by their ability to wash non-covalently bound enzyme from the support and their inability to influence the catalytic activity of the free enzyme in the performance of an assay reaction. Useful surfactants which have been employed with the enzymes bound in the present invention include nonionic polyalkylene oxide materials such as the Tritons surfactants (available from Rohm and Haas Co., Philadelphia, Pa.) and the Pluronic™ surfactants (available from BASF Corp., Parsippany, N.J.). These surfactant materials are efficacious when employed in aqueous solutions at concentrations from 0.001 to 3.0 weight percent, preferably 0.1 to 1.5 weight percent. After the enzyme/support adducts have been treated with these surfactant solutions for a period of 1 to 24 hours, preferably 3 to 16 hours, the heterogeneous mixtures may be filtered and the enzyme/support adducts washed with water to remove surfactant and any residual unbound enzyme. Finally, the prepared enzyme/support adducts may be stored as a slurry or suspension by adding a buffer solution which delivers a pH of optimum stability for the particular enzyme; slurries are refrigerated at 1° to 5° C. and are dispensed into reaction mixtures generally in an aliquot format. Alternatively, the washed enzyme/support adducts may be lyophilized, stored cold (−30° to 50° C.), and dispensed as dry solids.

It is also apparent to one skilled in the art that not all of the isocyanate groups are consumed in the binding process and may hydrolyze subsequently, especially when stored as an aqueous slurry.

Hydrolysis creates charged groups which can provide an indirect benefit after enzyme binding has occurred because water molecules can become attracted to the charged groups and provide a more hydrated medium. Other benefits include increased activity of the bound enzyme and increased catalyst lifetime.

Objectives of the invention include: 1) to covalently bind as much enzyme as possible; 2) to retain a highly active enzyme in the process; and 3) to provide a non-leaching catalyst with which to conduct synthetic organic reactions. In order to accomplish these objectives it has been determined that effective binding protocols and choices of particular supports employed must be adjusted somewhat to fit a given enzyme.

Pig Liver Esterase

Pig liver esterase (PLE; Carboxyl esterase, EC 3.1.1.1) was purchased from Sigma Chemical Co. (St. Louis, Mo.) as a suspension in 3.2M ammonium sulfate. Its specific activity was about 200 units per milligram protein (one unit is defined as the amount needed to hydrolyze one micromole of ethyl butyrate per minute at pH 8.0 at 25° C.). Before binding, the enzyme was first dialyzed against three changes of a solution consisting of 0.7M sodium citrate and 0.05M disodium hydrogen phosphate and 0.05M sodium hydrogen phosphate adjusted to pH 7.5. This procedure brought the enzyme to the desired pH and ionic strength and removed ammonium ions. The dialysate was then filtered through a 0.45 micron cellulosic syringe filter and the enzyme concentration determined spectrophotometrically using an extinction coefficient of 14.8 at 280 nm (1%, 1 cm). This was determined gravimetrically and is close to the value of 13.8 reported by Barker and Jencks in *Biochemistry*, 1969, 8, 3879–3889.

Spectrophotometric Assay: Into a 3 mL quartz cuvette were placed 2.4 mL of 50 mM EPPS (N-[2-hydroxyethyl] piperazine-N'-[3-propanesulfonic acid]; Sigma Chemical Co.) buffer at pH 8.0 and a magnetic cuvette stirring bar. The cuvette was placed in the thermostated stirring cuvette holder of a Hewlett Packard 8450A diode array spectrophotometer and allowed to equilibrate to 25° C. For free enzyme in solution, a 10 to 20 microliter aliquot was added to the cell followed by 80 microliters of a 1.0 mg/mL solution of p-nitrophenyl acetate in anhydrous acetonitrile. The linear rate of increase in absorbance at 400 nm (due to p-nitrophenolate generation), reported as milliabsorbance units per second, was a measure of the enzyme activity present. Enzyme concentration was adjusted so as to keep the measured rate below 25 milliabsorbance units per second. In this assay the esterase typically had a specific activity of 13–15 milliabsorbance units per second per microgram the activity of the immobilized enzyme was measured in the same manner except that 20 microliters of a 1.0% solids slurry of the support containing bound enzyme was used. Deviations in absorbance due to light scattering by support particles in the stirred cuvette averaged out during the course of the experiment and were not a problem. Typically, this assay using either free or bound enzyme was reproducible to within 10%. Data reported in the Examples section include averages of three trials of 20 microliter samples of "1st Filtrate" (a measure of the quantity of free enzyme remaining after exposure to the reactive supports), "Slurry" (the actual immobilized enzyme activity as described above), and "Supernatant" (an indication of leaching of non-covalently bound enzyme from the completely processed support catalyst). "1st Filtrate" samples were obtained by examining the filtrate obtained from the initial filtration (sintered glass, 10–20 micrometers) after exposure of the free enzyme solution to the reactive supports. Values are reported as milliabsorbance units per milligram of enzyme reacted, and those in parentheses refer to percentages of residual, unbound PLE remaining the original challenge (now referred to as 1st Filtrate). "Slurry" samples were obtained as described above by removing aliquots from well dispersed support particles in 0.5M EPPS (1.0% insoluble solids). "Supernatant" values were obtained after at least 24 hours after the 0.5M EPPS slurry had been prepared by examining the activity of the filtrate obtained by filtering a portion of the slurry using a 0.45 micron filter; percentages in parentheses indicate the level of supernatant activity contribution to the slurry value. Values reported for all three kinds of samples are corrected for small background autohydrolysis rates observed in the absence of enzyme under conditions of the assay.

Bacterial Lipase

Lipase PS-800 (glycerol ester hydrolase, EC 3.1.1.3) was obtained from Amano International Enzyme Co. (Troy, Va.) as a dry powder. Its stated specific activity was >800 units per milligram (in which one unit is defined as the amount of enzyme that will liberate 1 micromole of fatty acid from a triglyceride in one minute). The enzyme was suspended in phosphate-buffered saline (PBS; 0.85% NaCl (w/v), 0.01M sodium phosphate, pH 7.2) at a concentration of 2 mg/mL for binding studies.

Spectrophotometric Assay: The spectrophotometric assay for the determination of lipase activity was identical to that used for the determination of PLE activity, except the concentration of p-nitrophenyl acetate in the acetonitrile stock solution was increased to 20 mg/mL.

Penicillin Acylase

Penicillin acylase (PGA; penicillin amidohydrolase, ED 3.5.1.11) was purchased from Pharma Biotechnologie Hannover (Hannover, Germany) as a solution in 0.1M sodium phosphate, pH 7.5, with typical protein contents ranging from 60–70 mg/mL. Specific activities ranged from 17–24 Units/mg protein; one International Unit is defined as the amount of enzyme required to cleave one micromole of phenylacetic acid from penicillin G per minute at 37° C. and pH 7.8, as determined by titrating the released acid with sodium hydroxide. The enzyme was used as received.

Titrimetric Assay: Into a thermostated (37° C.) 30 mL beaker containing a magnetic stirring bar were pipetted 20 mL of a 2.0 wt % penicillin G solution, prepared by dissolving penicillin G (sodium salt, Sigma Chemical Co., St. Louis, Mo.) into a solution of 0.01M phosphate/0.01M sodium chloride at pH 7.8. A thermometer, pH electrode, and autotitrator bdret tip were then inserted. The pH of the resulting penicillin G solution was adjusted to 7.8 by addition of 0.1M sodium hydroxide.

Aliquots of PGA slurries and filtrates were adjusted so as to deliver a maximum of 200 micrograms of enzyme. Progress of the enzymatic reaction was monitored by titrating the liberated phenylacetic acid with standard sodium hydroxide solution. PGA aliquots were added directly to the penicillin G solution, and reaction rates were determined using a Mitsubishi GT 06 Automatic Titrator and 0.05M sodium hydroxide as titrant, and activities are expressed in International Units per milligram of enzyme charged.

In illustrating their utility as immobilizing media, for simplicity, since no cofactors, coenzymes, or other ancillary agents were required, only hydrolase enzymes were treated with the novel reactive supports of the invention. It should be apparent to anyone skilled in the art, however, that all major classes of enzymes including oxidoreductases, transferases, lyases, kinases, isomerases, ligases, and other hydrolases are amenable to immobilization employing the reactive supports and binding protocols disclosed herein. Furthermore, other biomacromolecules such as other proteins, lipoproteins, aminosaccharides, cells, antibodies, and antigens can be immobilized as well.

Objects and advantages of the invention are further illustrated by the following examples, but the particular materials and amounts thereof recited in the examples, as well as other conditions and details, should not be construed to unduly limit this invention.

COMPARATIVE EXAMPLE A

This comparative example teaches that the isocyanate groups are necessary for binding effective quantities of enzyme. Also, despite virtually quantitative hydrophobic binding of the PLE, the absences of significant activity in both the slurry and supernatant indicate very effective washing operations in the protocol.

The "T" homopolymer (100 mg), possessing no isocyanate groups and a surface area of 168 m²/g, was exposed to a solution comprising pig liver esterase (PLE; 4.0 mg dissolved in the citrate/phosphate medium described in the dialysis operation above), 6.0 mL of the 0.7M sodium citrate/0.1M sodium phosphate solution at pH 7.5, and 0.15 mL of a solution of 4% Pluronic™ L-31 polyalkylene oxide surfactant in water and tumbled at 22° C. for 2 hours. The mixture was filtered and washed with distilled water (3×). The filtercake was then resuspended in 1% Triton™ X-100 polyalkylene oxide surfactant in water, and the mixture was tumbled at 22° C. for 16 hours. This mixture was filtered, and the filtercake was washed with water (4×) and was stored in 10 mL of 0.5M EPPS at 4° C. Upon performing the assay reaction as described in the PLE section above, the "1st Filtrate" value was 0.1 indicating >99% of the PLE had been hydrophobically bound onto the "T" support. The slurry value, after the extensive washing procedures, was only 0.5, indicating the initial binding was virtually all hydrophobic and that the washing protocols were very efficient in removing non-covalently bound PLE; the supernatant was at the autohydrolysis background level of 0.1.

EXAMPLES 1–11

Employing the binding procedures described in Comparative Example A, the following examples broadly illustrate the invention. The importance of surface area of the supports and dispersion of the isocyanate groups can be seen by inspection of the 1st Filtrate column; when the surface area was <100 m²/g, significant quantities of PLE were left in the challenge solution. On the other hand, as indicated by both the low 1st Filtrate and slurry values in Table I, the more active catalysts were generally those possessing surface areas >100 m²/g, especially with ore hydrophilic polymer backbones. In no instance with the supports of the invention was leaching a significant problem.

TABLE I

| Ex. | Support | Surface Area (m²/g) | 1st Filtrate[A] | Slurry[B] | Supernatant[C] |
|---|---|---|---|---|---|
| 1 | E/20 | 116 | 1.1 (0.6%) | 12.1 | 0.1 (1%) |
| 2 | T/15DMA-15 | 89 | 49.0 (27%) | 9.9 | 0.5 (5%) |
| 3 | T/10PhOEM-50 | 48 | 45.2 (25%) | 3.5 | 0.2 (6%) |
| 4 | T/10DMA-10 | 130 | 0.2 (0.1%) | 4.0 | 0.0 (0%) |
| 5 | T/20 | 134 | 3.7 (2%) | 9.3 | 0.2 (2%) |
| 6 | T/20BMA-10 | 136 | 1.3 (0.7%) | 8.9 | 0.3 (3%) |
| 7 | T/20BMA-20 | 64 | 61.5 (34%) | 4.9 | 0.5 (10%) |
| 8 | T/10LMA-20 | 81 | 14.6 (8%) | 2.8 | 0.0 (0%) |
| 9 | D/20 | 345 | 1.5 (0.8%) | 11.3 | 0.1 (1%) |
| 10 | T/20HEMA-30 | 84 | 14.0 (8%) | 14.0 | 0.3 (2%) |
| 11 | T/20DMA-20 | 73 | 25.3 (14%) | 13.0 | 0.9 (7%) |

[A]: a measure of the quantity of free enzyme remaining after exposure to the reactive supports
[B]: actual immobilized enzyme activity
[C]: an indication of leaching of non-covalently bound enzyme from the completely processed support catalyst

COMPARATIVE EXAMPLES B–D

PLE binding was conducted with the comparative example supports employing the same protocol as described in Examples 1–11. The data in TABLE II, below indicate that very low surface areas resulted when crosslinking monomers were omitted. Even when relatively high concentrations of the isocyanate-functional monomer were employed, e.g., up to 80 wt %, most of the PLE was left unbound in the challenge solution and a poor catalyst resulted.

TABLE II

| Ex. | Support | Surface Area (m²/g) | 1st Filtrate[A] | Slurry[B] | Supernatant[C] |
|---|---|---|---|---|---|
| B | 20MMA-80 | 9 | 112 (62%) | 2.3 | 0.2 (9%) |
| C | 40MMA-60 | 8 | 152 (88%) | 1.5 | 0.3 (20%) |
| D | 80DMA-20 | 4 | 124 (71%) | 1.3 | 0.2 (15%) |

A, B, C as defined for TABLE I.

EXAMPLES 12–15

These examples teach that a desirable loading of PLE on the supports is 4–5 weight percent. At higher concentrations, the PLE was not removed completely by the reactive supports, and leaching was discernible.

The "T/20" support (100 mg) was challenged with 2, 4, 6, and 8 wt % PLE employing the protocol outlined with examples 1–11. The data is shown in TABLE III, below.

TABLE III

| Ex. | PLE Wt % | 1st Filtrate^A | Slurry^B | Supernatant^C |
|---|---|---|---|---|
| 12 | 2.0 | 0 | 8.3 | 0 |
| 13 | 4.0 | 0.2 | 11.4 | 0 |
| 14 | 6.0 | 1.7 | 14.2 | 0.3 |
| 15 | 8.0 | 21.8 | 14.8 | 0.5 |

$^{A,B,C}$as defined for TABLE I

EXAMPLES 16–19

These examples teach that a preferred isocyanate content in the supports of the invention is about 10 weight percent, although the entire range of concentrations examined from 5 to 20 wt % performed acceptably well.

The supports in TABLE IV below were formulated to maintain an approximately constant support lipophilicity as the IEM concentration varied; PLE binding was conducted as described in Examples 1–11. The data is shown in TABLE IV.

TABLE IV

| Ex. | Designation | 1st Filtrate^A | Slurry^B | Supernatant^C |
|---|---|---|---|---|
| 16 | T/5HEMAC-11.5 | 0 | 13.7 | 0 |
| 17 | T/10HEMAC-7.6 | 0 | 15.5 | 0 |
| 18 | T/15HEMAC-4 | 0 | 16.0 | 0 |
| 19 | T/20 | 0.3 | 13.0 | 0 |

$^{A,B,C}$as defined for TABLE I

EXAMPLES 20–21

To 100 mg samples of the isocyanate-functional supports listed in the table below were added 2.0 mL of the lipase solution consisting of 4.0 mg of lipase in 4.0 mL of PBS, 4.0 mL of PBS, and Pluronic™ L-31 polyalkylene oxide surfactant (18 mg). Mixtures were tumbled at room temperature for 18 hours. After filtering to obtain "1st Filtrates", filtercakes were washed with deionized water (3×) and were resuspended in 10 mL of PBS also containing 1% Triton™ X-100 polyalkylene oxide surfactant to remove any unbound enzyme. After tumbling for 5 hours, the mixtures were filtered and the filtercakes were washed with water (4×). Finally, the solids were resuspended in 10 mL of 0.5 M EPPS buffer and stored at 4° C. to await activity determination. The data is shown in TABLE V below.

TABLE V

| Ex. | Designation | 1st Filtrate^A | Slurry^B | Supernatant^C |
|---|---|---|---|---|
| 20 | T/20 | 1.0(6%) | 13.2 | 0 |
| 21 | E/20 | 0.3(2%) | 7.5 | 0 |

$^{A,B,C}$as defined for TABLE I

EXAMPLES 22–23

To evaluate PGA binding capabilities of the various supports, 100 mg samples of the supports were exposed to 4 wt % PGA in 6.0 mL of 1.0M sodium citrate/0.1M phosphate buffer at pH 7.4 also containing 0.33 w/v % Pluronic L-31 polyalkylene oxide surfactant. Mixtures were contained in 15 mL vials and were tumbled at 22° C. for 2.5 hours. The mixtures were filtered (sintered glass 10–20 micrometers) (the filtrate was assayed for PGA activity to determine quantity of free enzyme remaining after exposure to the reactive support) and the filtercakes were rinsed with PBS (pH 7.2; 2×10 mL) and water (2×10 mL). The collected supports were then resuspended in a solution of 0.01M EPPS/0.01M sodium chloride, pH 7.5 (10 mL) for storage. This slurry was assayed to determine immobilized PGA activity, and the slurry supernatant, obtained by filtering a portion of the slurry with a 0.45 micron filter, was assayed to determine the level of leaching of non-covalently bound PGA. The data is shown in TABLE VI, below.

TABLE VI

| Ex. | Support | 1st Filtrate^A | Slurry^B | Supernatant^C |
|---|---|---|---|---|
| 22 | T/20 | 0.5(2.5%) | 12.7 | 0.4 |
| 23 | E/20 | 0.5(2.5%) | 11.1 | 0.3 |

$^{A, B, C}$ as defined for TABLE I

Various modifications and alterations of this invention will become apparent to those skilled in the art without departing from the scope and spirit of this invention, and it should be understood that this invention is not to be unduly limited to the illustrative embodiments set forth herein.

We claim:

1. A method for preparing a crosslinked isocyanate-functional polymer support comprising the steps of
   a) copolymerizing an admixture comprising at least one ethylenically unsaturated isocyanate functional monomer and at least one polyethylenically unsaturated crosslinking monomer, a free-radical initiator for said monomers, and a solvent for said monomers, said initiator being unreactive with said monomers and polymerization products thereof, and
   b) isolating the resultant crosslinked isocyanate-functional polymer support that is insoluble in both aqueous and organic media.

2. The method according to claim 1 wherein said admixture further comprises at least one of hydrophilic and lipophilic monomers different from said monomers of a).

3. The method according to claim 1 wherein the weight ratio of total monomers to said solvent is present in the range of 1:5 to 1:10.

4. The method according to claim 1 further comprising the step of reacting said polymer support with an aqueous solution comprising a protein to provide a polymer support/protein conjugate.

5. The method according to claim 1 further comprising the step of reacting said polymer support with an aqueous solution comprising a biomacromolecule to provide a polymer support/biomacromolecule conjugate.

6. The method according to claim 4 wherein said protein is an enzyme.

7. The method according to claim 1 wherein in said admixture said isocyanate functional monomer is present in an amount in the range of 1 to 99 parts by weight and said crosslinking monomer is present in an amount of in the range of 99 to 1 parts by weight.

8. The method according to claim 1 wherein said admixture further comprises more than 0 to 98 parts by weight of other copolymerizable monomers.

9. The method according to claim 8 wherein said copolymerizable monomer in said admixture is at least one of hydrophilic and lipophilic.

10. The method according to claim 1 wherein said admixture further comprises an effective amount of a dispersion polymerization stabilizing agent.

11. The method according to claim 1 wherein said free radical initiator in said admixture is selected from the group consisting of azobis(iso-butyronitrile), benzoyl peroxide, lauryl peroxide, t-butyl peroxypivalate, and azobis(1-cyclohexanecarbonitrile).

12. The method according to claim 1 wherein said isocyanate-funcitonal monomer in said admixture comprises an isocyanatoalkyl ester of an ethylenically unsaturated carboxylic acid.

13. The method according to claim 1 wherein said isocyanate-functional monomer in said admixture is selected from the group consisting of 2-isocyanatoethyl acrylate, 2-isocyanatoethyl methacrylate, and methacryloyl isocyanate.

14. The method according to claim 1 wherein said polyethylenically unsaturated crosslinking monomer in said admixture is selected from the group consisting of a polyethylenically unsaturated ester, a polyethylenically unsaturated amide, and a polyvinyl benzene derivative.

15. The method according to claim 1 wherein said resultant polymer support has a surface area of at least 20 square meters per gram.

16. The polymer support according to claim 1 having a surface area in the range of 50 to 350 square meters per gram.

17. The method according to claim 1 wherein said resultant crosslinked isocyanate-functional polymer support is a particle.

18. The method according to claim 17 wherein said resultant particle is a powder.

19. The method according to claim 1 wherein the resultant polymer support is a cluster of beads.

20. The method according to claim 19 wherein said cluster of beads comprises regularly or irregularly shaped beads, and wherein said regularly shaped beads are symmetric about a planar axis.

21. The method according to claim 17 wherein said particle is a filamentous agglomerated particle.

22. The method according to claim 19 wherein said agglomerated particle has a size in the range of 10 to 1000 micrometers.

23. A method of catalyzing a reaction comprising the step of reacting an insoluble supported catalyst with a complementary coreactant, said insoluble supported catalyst comprising an insoluble polymer support including isocyanate groups or hydrolysis products thereof dispersed on a crosslinked polymeric backbone, said polymer support being insoluble in both aqueous and organic media and being derived from polvethylenically unsaturated monomers by free radical polymerization and having at least one biomacromolecule covalently bound thereto, said insoluble polymer support being a particle.

* * * * *

UNITED STATES PATENT AND TRADEMARK OFFICE
CERTIFICATE OF CORRECTION

PATENT NO.: 5,760,152

DATED: June 2, 1998

INVENTOR(S): Steven M. Heilmann, Gary J. Drtina, Louis C. Haddad, Frederick W. Hyde, Dean M. Moren, and Robert A. Pranis It is certified that error appears in the above-identified patent and that said Letters Patent is hereby corrected as shown below:

Col. 2, line 30, "Olyureas" should read -- polyureas --
Col. 4, line 34, "*Micronecansulation*" should read -- *Microencapsulation* --
Col. 4, Line 57, ""wetted"0" should read -- "wetted"--
Col. 7, Line 21, "Pluronicm$^{TM}$" should read -- Pluronic$^{TM}$ --
Col. 8, Line 39, "staple." should read -- stable. --
Col. 8, Line 43, "olyanionic" should read -- polyanionic --
Col. 9, line 15, "50°" should read --5°--
Col. 11, Line 7, "bdret" should read -- buret --
Col. 12, Line 9, "ore" should read -- more --
Col. 16, Line 23, "polvethylenically" should read -- polyethylenically --

Signed and Sealed this

Sixth Day of October, 1998

BRUCE LEHMAN

Attest:

Attesting Officer

Commissioner of Patents and Trademarks